United States Patent [19]

Feinstein et al.

[11] 4,066,622

[45] Jan. 3, 1978

[54] POLYAMIDE ACIDS AND POLYESTERIMIDES FROM 1,3-ADAMANTYLENE-BIS-TRIMELLITATE DIANHYDRIDES

[75] Inventors: Allen Feinstein, Wheaton; Ellis K. Fields, River Forest, both of Ill.

[73] Assignee: Standard Oil Company, Chicago, Ill.

[21] Appl. No.: 657,442

[22] Filed: Feb. 12, 1976

Related U.S. Application Data

[62] Division of Ser. No. 597,339, July 21, 1975, Pat. No. 3,976,665.

[51] Int. Cl.² ............................................. C08G 73/16
[52] U.S. Cl. ............................. 260/47 CP; 260/75 N; 260/78 TF
[58] Field of Search ................ 260/78 TF, 47 CP, 65, 260/75 N

[56] References Cited

U.S. PATENT DOCUMENTS

| 3,814,735 | 6/1974 | Thompson | 260/65 |
|---|---|---|---|
| 3,847,872 | 11/1974 | Thompson | 260/65 |

*Primary Examiner*—Lester L. Lee
*Attorney, Agent, or Firm*—Gregory E. Croft; Arthur G. Gilkes; William T. McClain

[57] ABSTRACT

Novel dianhydrides derived from trimellitic anhydride and adamantane diacetates are polymerized with a diamine to produce the corresponding polyamide, which is subsequently converted to the polyesterimide by heat treatment at temperatures above 500° F.

8 Claims, No Drawings

POLYAMIDE ACIDS AND POLYESTERIMIDES FROM 1,3-ADAMANTYLENE-BIS-TRIMELLITATE DIANHYDRIDES

This is a division, of application Ser. No. 597,339, filed July 21, 1975 now U.S. Pat. No. 3,976,665.

BACKGROUND OF THE INVENTION

1. Field of the Invention

This invention relates to polyimides and their precursors. More specifically, this invention relates to polyimides, polyamides, and dianhydrides derived from trimellitic anhydride and adamantane diacetates.

2. Description of the Prior Art

A first patent issued to D. F. Loncrini, U.S. Pat. No. 3,182,073 (1965) discloses the preparation of polyanhydrides of the general formula

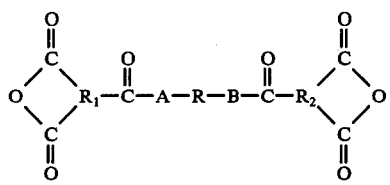

in which A and B can be oxygen, $R_1$ and $R_2$ can be phenyl radicals, and R can be an alicyclic radical such as the divalent radical derived from cyclohexane, cyclobutane, cyclopentane, and the like.

A second patent also issued to Loncrini, U.S. Pat. No. 3,355,427 (1967), which incorporates the U.S. Pat. No. 3,182,703 by reference, dislcoses the preparation of polyamides and polyimides from diamines and the polyanhydrides disclosed in the U.S. Pat. No. 3,182,703. Reference is broadly made to the use of alicyclic compounds mentioned in the U.S. Pat. No. 3,182,703.

However, neither patent contains an enabling disclosure where an alicyclic compound is used to produce a dianhydride, a polyamide, or a polyesterimide. More specifically, the use of an adamantane derivative is not suggested. In fact, those alicyclic compounds which are cited as exemplary are all monocyclic compounds of the same homologous series and are structurally dissimilar to the adamantane derivatives. Because the geometry of the adamantane nucleus will not allow the formation of a double bond between the α and β carbon atoms, adamantane derivatives are unique in that they cannot undergo ester pyrolysis which can readily occur with other alicyclic nuclei such as cyclohexane. This fact coupled with the marked structural difference between Applicant's compositions and those of the prior art are believed to give rise to desirable physical properties such as high heat stability. The polyesterimides are particularly useful for making films, coatings, and molded forms for use at elevated temperatures.

Accordingly, it is an object of this invention to produce a polyesterimide incorporating the adamantane nucleus which is useful for making films, coatings and molded forms for use at elevated temperatures.

It is a further object of this invention to produce a polyamide acid incorporating the adamantane nucleus which is useful in preparing temperature resistant polyesterimides.

It is a further object of this invention to produce a dianhydride incorporating the adamantane nucleus which is useful in preparing temperature resistant polyesterimides.

SUMMARY OF THE INVENTION

In one aspect, the invention resides in a new and useful dianhydride having the general formula

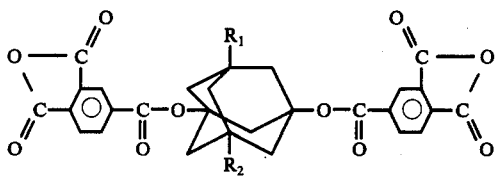

wherein $R_1$ and $R_2$ are individually selected from the group consisting of hydrogen, an alkyl radical, and an aryl radical. Groups $R_1$ and $R_2$ can be the same or different.

In a further aspect, the invention resides in a new and useful polyamide acid formed by reacting the above-mentioned dianhydride with a diamine, said diamine having the general formula $$H_2N-R_3-NH_2$$

wherein $R_3$ is selected from the group consisting of alkylene, arylene, or heterocyclic groups.

In a further aspect, the invention resides in a new and useful polyesterimide formed by reacting the above-mentioned dianhydride with the above-mentioned diamine and heating the reaction product to a temperature of at least 500° F.

DESCRIPTION OF THE PREFERRED EMBODIMENT

We have found that the diacetate of adamantane having the general formula

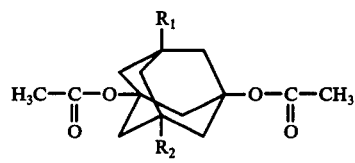

reacts with trimellitic anhydride under the conditions of the transacidolysis reaction described by Hirsch et al. in U.S. Pat. No. 3,183,248 (1965) to give the corresponding dianhydride. $R_1$ and $R_2$ can be hydrogen, alkyl groups, or aryl groups such as methyl, ethyl, isopropyl, n-propyl, t-butyl, phenyl, biphenyl, or naphthyl groups. The dianhydride can then be polymerized with a diamine of the general formula $$H_2N-R_3-NH_2$$

wherein $R_3$ can be arylene, alkylene, or heterocyclic groups. The resultant polyamide acid can then be subsequently converted to the polyesterimide by heat treatment at temperatures above 500° F., preferably between 500° to 700° F.

EXAMPLE

A solution of 3.87 grams of 1,3-dihydroxyadamantane diacetate and 5.57 grams of trimellitic anhydride was heated at 200°-235° C for 4 hours. The acetic acid generated in the reaction (1.7 grams) was continuously distilled as the reaction proceeded. The reaction mixture was then dissolved in benzene and filtered. The filtrate afforded 3.5 grams of yellow crystals upon being concentrated. A benzene solution of the crystals was heated with charcoal followed by three recrystallizations to yield 1.8 grams of 1,3-adamantylene-bis-trimellitate dianhydride. The anhydride had an uncorrected melting point of 192°–193° C.

A stirred solution of 0.58 grams 4,4'-diaminodiphenyl ether in 9.6 grams N-methyl pyrrolidone was prepared, to which 1.5 grams of the above-mentioned dianhydride was slowly added over a period of 15 minutes. The reaction mixture was stirred for one hour to produce the polyamide acid. The resulting solution had a Gardner Viscosity of 5.5 stokes.

A film cast from the polyamide solution and heated at 600° F for 5 minutes yielded a thermally stable flexible polyesterimide, which, after curing at 300° C. for 16 hours, had a glass transition temperature of 235° C. and did not begin to decompose during thermal gravimetric analysis until heated beyond 390° C.

It will be obvious to those skilled in the art that many variations of the preferred embodiment may be made without departing from the scope of this invention.

We claim:

1. As a composition of matter, a polyamide acid formed by reacting about equimolar amounts of a dianhydride with a diamine at a temperature below 500° F., said dianhydride having the general formula

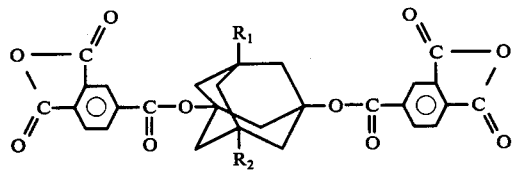

wherein $R_1$ and $R_2$ are individually selected from the group consisting of hydrogen, an alkyl radical, and an aryl radical, and said diamine having the general formula

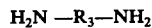

wherein $R_3$ is selected from the group consisting of alkylene and arylene groups.

2. The polyamide acid of claim 1 wherein $R_1$ is hydrogen.

3. The polyamide acid of claim 2 wherein $R_2$ is hydrogen.

4. As a composition of matter, the polyamide acid produced by reacting about equimolar amount of 1,3-adamantylene-bistrimellitate dianhydride with 4,4'-diaminodiphenyl ether at a temperature below 500° F.

5. As a composition of matter, a polyestermide formed by reacting about equimolar amounts of a dianhydride with a diamine and heating the reaction product to a temperature of from 500° F. to 700° F., said dianhydride having the general formula

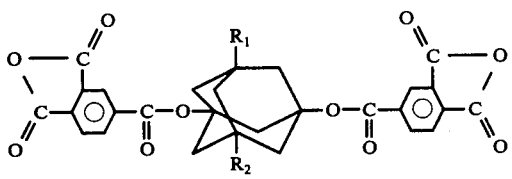

wherein $R_1$ and $R_2$ are individually selected from the group consisting of hydrogen, an alkyl radical, and an aryl radical, and said diamine having the general formula $$H_2N-R_3-NH_2$$

wherein $R_3$ is selected from the group consisting of alkalene and arylene groups.

6. The polyesterimide of claim 5 wherein $R_1$ is hydrogen.

7. The polyesterimide of claim 6 wherein $R_2$ is hydrogen.

8. As a composition of matter, a polyesterimide formed by reacting about equimolar amounts of 1,3-adamantylene-bistrimellitate dianhydride with 4,4'-diaminodiphenyl ether and subsequently heating the reaction product to a temperature of from 500° F. to 700° F.

* * * * *

UNITED STATES PATENT OFFICE
CERTIFICATE OF CORRECTION

Patent No. 4,066,622          Dated January 3, 1978

Inventor(s) Feinstein, Allen; Fields, Ellis K.

It is certified that error appears in the above-identified patent and that said Letters Patent are hereby corrected as shown below:

Column 1, line 34 )
Column 1, line 36 )    "U.S. Pat. No. 3,182,703" should
Column 1, line 38 )      read ---- 3,182,073 --.

Signed and Sealed this

Twentieth Day of June 1978

[SEAL]

Attest:

RUTH C. MASON
Attesting Officer

DONALD W. BANNER
Commissioner of Patents and Trademarks